United States Patent [19]

Sowin et al.

[11] Patent Number: 5,362,912
[45] Date of Patent: Nov. 8, 1994

[54] PROCESS FOR THE PREPARATION OF A SUBSTITUTED DIAMINODIOL

[75] Inventors: Thomas J. Sowin, Grayslake; Steven M. Hannick, Highland Park, both of Ill.; Elizabeth M. Doherty, New Haven, Conn.; Takahiro Sato, Tokyo; Takayuki Suzuki, Kanagawa, both of Japan

[73] Assignee: Abbott Laboratories, Abbott Park, Ill.

[21] Appl. No.: 48,921

[22] Filed: Apr. 23, 1993

Related U.S. Application Data

[63] Continuation-in-part of Ser. No. 885,575, May 19, 1992, abandoned, which is a continuation-in-part of Ser. No. 746,020, Aug. 15, 1991, abandoned, which is a continuation-in-part of Ser. No. 616,170, Nov. 20, 1990, abandoned, which is a continuation-in-part of Ser. No. 518,730, May 9, 1990, Pat. No. 5,142,056, which is a continuation-in-part of Ser. No. 456,124, Dec. 22, 1989, abandoned, which is a continuation-in-part of Ser. No. 405,604, Sep. 8, 1989, abandoned, which is a continuation-in-part of Ser. No. 355,945, May 23, 1989, abandoned.

[51] Int. Cl.$^5$ ............................................. C07C 213/00
[52] U.S. Cl. ................................................... 564/360
[58] Field of Search ........................................ 564/360

[56] References Cited

FOREIGN PATENT DOCUMENTS

| 402646 | 12/1990 | European Pat. Off. |
| 428849 | 5/1991 | European Pat. Off. |
| 486948 | 5/1992 | European Pat. Off. |
| 503561 | 9/1992 | European Pat. Off. |
| WO91/18866 | 12/1991 | WIPO |
| WO92/00948 | 1/1992 | WIPO |
| WO92/06996 | 4/1992 | WIPO |

OTHER PUBLICATIONS

Kondradi et al "Pinacol Homocouping of . . . " CA116(5):40555e. J. Org. Chem. 57(1), pp. 28–32. 1992.
Konradi, et al., J. Org. Chem 57 28 (1992).
Kano, et al., Tetrahedron Letters 6331 (1987).
Sakaitani, et al., J. Am. Chem. Soc. 112 1150 (1990).
Konradi, et al., J. Org. Chem. 55 4506 (1990).

Primary Examiner—Marianne M. Cintins
Assistant Examiner—Keith MacMillan
Attorney, Agent, or Firm—Stephen R. Crowley

[57] ABSTRACT

A process is disclosed for the preparation of a substituted diaminodiol.

10 Claims, No Drawings

PROCESS FOR THE PREPARATION OF A SUBSTITUTED DIAMINODIOL

This invention was made with Government support under contract number AI27220 awarded by the National Institute of Allergy and Infectious Diseases. The Government has certain rights in this invention.

This is a continuation-in-part of U.S. patent application Ser. No. 885,575, filed May 19, 1992, now abandoned, which is a continuation-in-part of U.S. patent application Ser. No. 746,020, filed Aug. 15, 1991, now abandoned, which is a continuation-in-part of U.S. patent application Ser. No. 616,170, filed Nov. 20, 1990, now abandoned, which is a continuation-in-part of U.S. patent application Ser. No. 518,730, filed May 9, 1990, now U.S. Pat. No. 5,142,056, which is a continuation-in-part of U.S. patent application Ser. No. 456,124, filed Dec. 22, 1989, now abandoned, which is a continuation-in-part of U.S. patent application Ser. No. 405,604, filed Sep. 8, 1989, now abandoned, which is a continuation-in-part of U.S. patent application Ser. No. 355,945, filed May 23, 1989, now abandoned.

TECHNICAL FIELD

The present invention relates to a process for the preparation of a substituted diaminodiol.

BACKGROUND OF THE INVENTION

Compounds which are inhibitors of HIV protease are currently being investigated for treatment of HIV infection. Certain HIV protease inhibitors comprise a moiety which is a substituted 2,5-diamino-3,4-dihydroxyhexane. HIV protease inhibitors of particular interest are compounds of the formula 1:

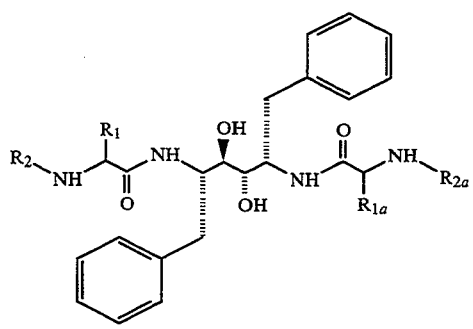

wherein $R_1$ and $R_{1a}$ are independently selected from loweralkyl and $R_2$ and $R_{2a}$ are independently selected from $-C(O)-R_4-R_5$ wherein at each occurrence $R_4$ is independently selected from O, S and $-N(R_6)-$ wherein $R_6$ is hydrogen or loweralkyl and at each occurrence $R_5$ is independently selected from pyridyl or (pyridyl)alkyl; or a pharmaceutically acceptable salt, prodrug or ester thereof. Compounds of formula 1 are disclosed in European Patent Application No. EP0402646, published Dec. 19, 1990.

A preferred HIV protease inhibitor is a compound of formula 2:

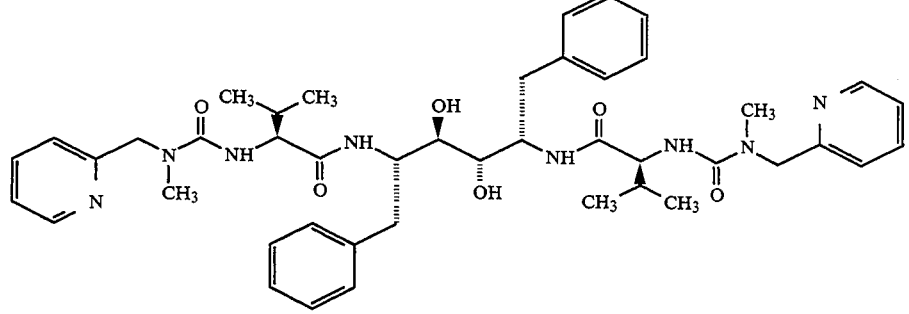

or a pharmaceutically acceptable salt, prodrug or ester thereof.

DISCLOSURE OF THE INVENTION

The present invention relates to an intermediate which is useful for the preparation of compounds of formula 1 and 2. The intermediate is a compound of formula 3:

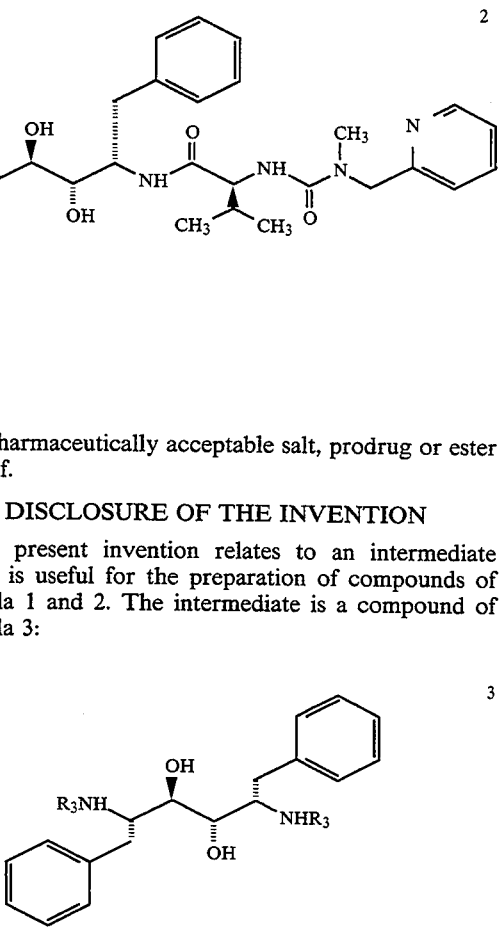

wherein $R_3$ at each occurrence is independently selected from hydrogen and an N-protecting group; or a salt thereof.

The present invention also relates to a process for the preparation of a compound of formula 3.

A process for the preparation of 3 is shown in Schemes I and II. Scheme I illustrates the preparation of diol 7. Esterification of L-phenylalanine (for example, methanol/SOCl$_2$ or methanol/HCl and the like) provides phenylalanine ester acid addition salt (for example, phenylalanine methyl ester hydrochloride and the like). N-protection with a carbamate protecting group (for example, by reaction with R"OC(O)Cl or (R"OC-(O))$_2$O (wherein R" is loweralkyl or benzyl) and the like in the presence of a base such as sodium carbonate or sodium bicarbonate and the like in a solvent such as chloroform or CH$_2$Cl$_2$ and the like) provides N-protected phenylalanine ester (for example, N-carbonylbenzyloxy phenylalanine ester and the like). Reduction of the ester (for example, with lithium aluminum hydride or NaBH$_4$/acetic acid and the like in an inert solvent such as tetrahydrofuran or methyl t-butyl ether and the like at a temperature of from about −60° C. to about 90° C.) provides primary alcohol 5 ($R_3$ is R*OC(O)— wherein R* is benzyl or loweralkyl and the like).

Oxidation of alcohol 5 (for example, by reaction with oxalyl chloride/dimethylsulfoxide in methylene chloride at about −60° C. or with $SO_3$/pyridine or with TEMPO/NaOCl and the like) gives aldehyde 6. Reaction of aldehyde 6 with a mixture of $VCl_3(THF)_3$ and zinc dust (from about 0.5 equivalents to about 1.4 equivalents of zinc, based on vanadium) ($[V_2Cl_3(THF)_6]_2[Zn_2Cl_6]$) in an inert solvent (for example, methylene chloride or 1,2-dichloroethane and the like) at about room temperature provides a mixture of the (3R,4R), (3S,4S) and (3R,4S) diols. Reaction of the mixture of diols with acetone/$H_2SO_4$ provides a mixture of acetonides. The acetonide resulting from the (3S,4S) diol selectively crystallizes and precipitates out of solution and can be removed by filtration. The crude mixture of acetonides resulting from the (3R,4R) diol and (3R,4S) diol is reacted with methanolic HCl and the acetonide resulting from the (3R,4R) diol is selectively cleaved, causing the (3R,4R) diol 7 to selectively crystallize and precipitate.

Alternatively, water (in a ratio of from about 1:1 to about 1:2 (preferrably, about 1:1.5) water/acetone (w/w)) is added to the acetone/$H_2SO_4$ solution containing the crude mixture of acetonides of the (3R,4R) diol and (3R,4S) diol. This mixture is stirred for about 18 hours with heating to a temperature of between from about room temperature to about 60° C. for about 18 hours. After cooling to about room temperature, the (3R,4R) diol 7 selectively crystallizes and precipitates and is isolated by filtration. This alternative process allows for the preparation of pure (3R,4R) diol 7 without the isolation of intermediates.

Scheme II illustrates the conversion of 7 to 3. Protection of one of the hydroxyls of 7 is accomplished by reaction with $R_7C(OR_8)_3$ (wherein $R_7$ is hydrogen, loweralkyl, phenyl or benzyl and $R_8$ is loweralkyl), followed by aqueous hydrolysis. For example, acetylation by reaction with triethylorthoacetate/methanesulfonic acid in acetonitrile or tetrahydrofuran and the like), followed by aqueous hydrolysis provides 8 ($R_7$ is $CH_3$). The free hydroxyl group of 8 is converted into a sulfonate leaving group (for example, mesylate, triflate or tosylate and the like). Reaction of 8 with a sulfonylating agent $R^{}SO_2Cl$ or $(R^{}SO_2)_2O$ wherein $R^{**}$ is methyl, trifluoromethyl or 4-methylphenyl gives the sulfonate derivative of 8. For example, reaction of 8 with methanesulfonyl chloride or methanesulfonic anhydride and triethylamine/dimethylaminopyridine in an inert solvent such as methylene chloride or tetrahydrofuran and the like at a temperature of from about −50° C. to about 80° C. gives the methanesulfonate (mesylate) derivative of 8. When the sulfonate derivative of 8 is heated at a temperature of from about 50° C. to about 180° C. in a solvent such as dimethylformamide or acetonitrile and the like, 9 is obtained. This reaction is facilitated by addition of a soluble source of chloride, bromide or iodide ion, for example, $NH_4X$, LiX, NaX, KX, tetralkylammoniumX and the like (wherein X is Cl, Br or I). A preferred source of chloride, bromide or iodide ion is an aqueous solution of ammonium chloride, ammonium bromide or ammonium iodide, respectively. Reaction of 9 with an aqueous solution of strong base (for example, barium hydroxide octahydrate or NaOH/KOH and the like) in an inert solvent (for example, 1,4-dioxane or dimethoxyethane and the like) at a temperature of from about 25° C. to about 120° C. provides 3 ($R_3$ is hydrogen).

In a preferred embodiment of the invention $R_3$ is benzyloxycarbonyl and $R_7$ is $CH_3$.

Scheme III illustrates the preparation of the preferred intermediate (14) useful for reaction with 3 to provide 2. 2-Picolinaldehyde (10) is reacted with methylamine, followed by hydrogenation, to provide 2-(N-methyl)aminomethylpyridine (11). Reaction of 11 with the methyl or benzyl ester of N-phenoxycarbonyl-L-valine (12) provides 13. Hydrolysis (R=Me) or hydrogenation (R=benzyl) of 13 provides 14.

Standard peptide coupling reaction of 14 with 3 ($R_3$ is H) provides 2.

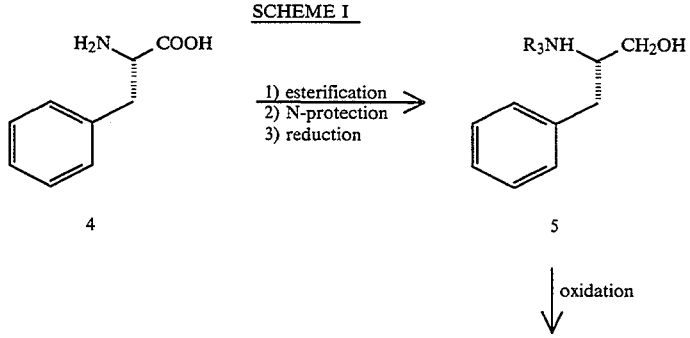

SCHEME I

SCHEME I
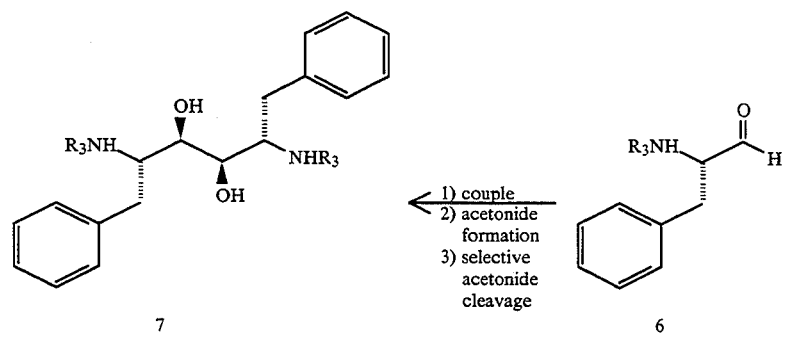
SCHEME II
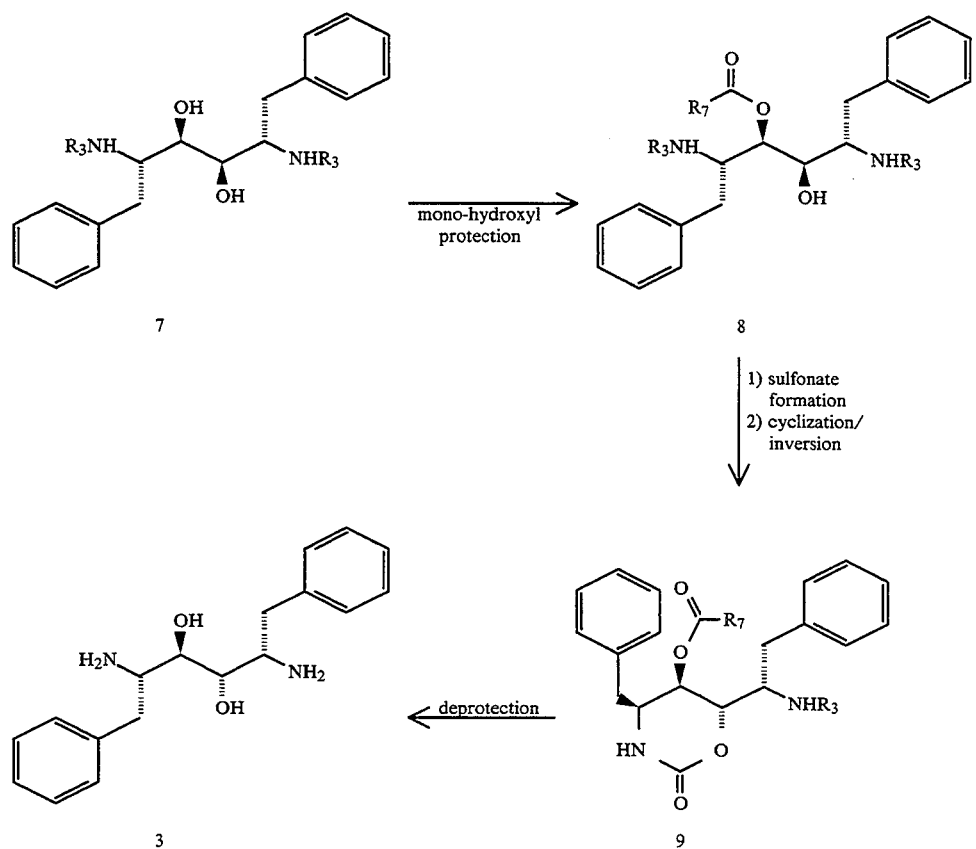
SCHEME III
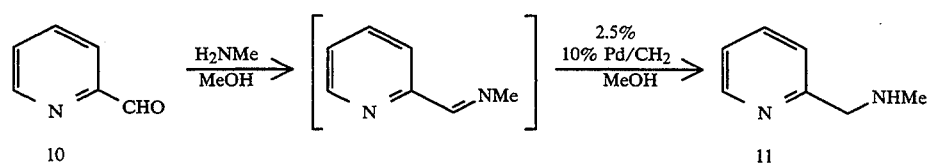

-continued
SCHEME III

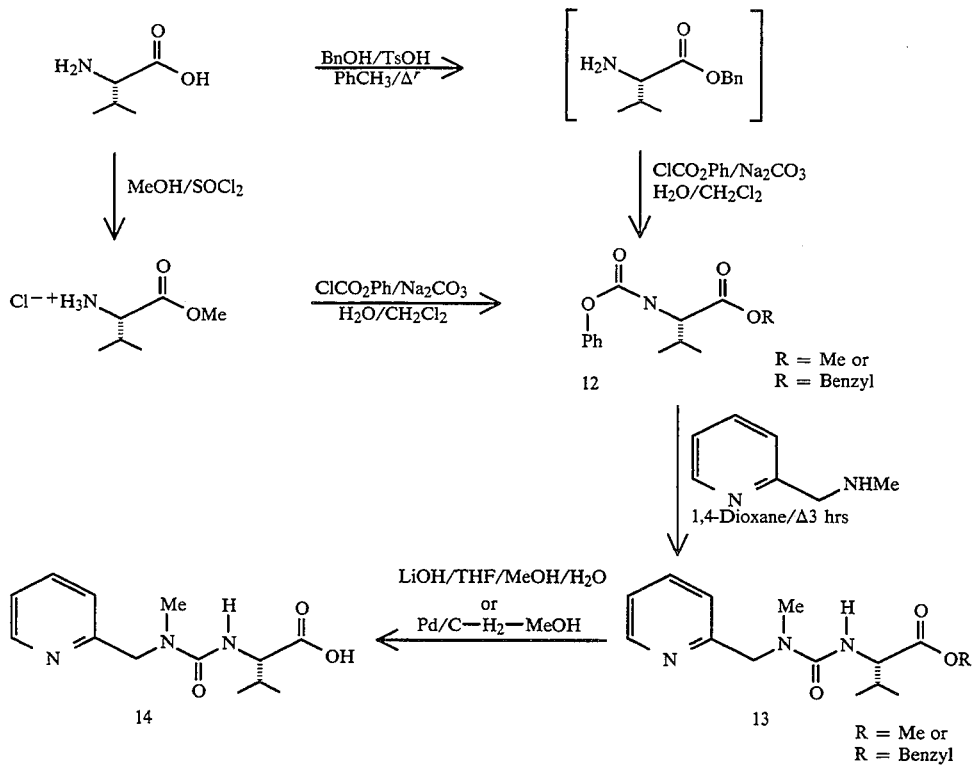

The term "loweralkyl" as used herein refers to straight or branched chain alkyl radicals containing from 1 to 6 carbon atoms including, but not limited to, methyl, ethyl, n-propyl, iso-propyl, n-butyl, iso-butyl, sec-butyl, n-pentyl, 1-methylbutyl, 2,2-dimethylbutyl, 2-methylpentyl, 2,2-dimethylpropyl, n-hexyl and the like.

The term "(pyridyl)alkyl" as used herein refers to a loweralkyl radical to which is appended a pyridyl group including, but not limited to, 2-pyridylmethyl, 3-pyridylmethyl, 4-pyridylmethyl, 2-pyridylethyl, 3-pyridylethyl, 4-pyridylethyl and the like.

The term "N-protecting group" or "N-protected" as used herein refers to those groups intended to protect an amino group against undersirable reactions during synthetic procedures. Commonly used N-protecting groups are disclosed in Greene, "Protective Groups In Organic Synthesis," (John Wiley & Sons, New York (1981)), which is hereby incorporated by reference. N-protecting groups comprise carbamates, amides, N-alkyl derivatives, amino acetal derivatives, N-benzyl derivatives, imine derivatives, enamine derivatives and N-heteroatom derivatives. N-protecting groups include formyl, acetyl, benzoyl, pivaloyl, t-butylacetyl, phenylsulfonyl, benzyl, t-butyloxycarbonyl (Boc), benzyloxycarbonyl (Cbz) and the like.

The compounds of the formula 1 and 2 can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, p-toluenesulfonate and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Other salts include salts with alkali metals or alkaline earth metals, such as sodium, potassium, calcium or magnesium or with organic bases.

Preferred salts of the compounds of the formula 1 and 2 include hydrochloride, methanesulfonate, sulfonate, phosphonate and isethionate.

The compounds of the formula 1 and 2 can also be used in the form of esters. Examples of such esters include a compound of formula 1 or 2 which has been acylated with a blocked or unblocked amino acid residue, a phosphate function, a hemisuccinate residue, an acyl residue of the formula R*C(O)— or R*C(S)— wherein R* is hydrogen, loweralkyl, haloalkyl, alkoxy, thioalkoxy, alkoxyalkyl, thioalkoxyalkyl or haloalkoxy, or an acyl residue of the formula $R_a$—C($R_b$)($R_d$)—C(O)— or $R_a$—C($R_b$)($R_d$)—C(S)— wherein $R_b$ and $R_d$ are independently selected from hydrogen or loweralkyl and $R_a$ is $-N(R_e)(R_f)$, $OR_e$ or $-SR_e$ wherein $R_e$ and $R_f$ are independently selected from hydrogen, loweralkyl and haloalkyl, or an aminoacyl residue of the formula $R_{180}NH(CH_2)_2NHCH_2C(O)-$ or $R_{180}NH(CH_2)_2OCH_2C(O)-$ wherein $R_{180}$ is hydrogen, loweralkyl, arylalkyl, cycloalkylalkyl, alkanoyl, benzoyl or an α-amino acyl group. The amino acid esters of particular interest are glycine and lysine; however, other amino acid residues can also be used, including those wherein the amino acyl group is $-C(O)CH_2NR_{200}R_{201}$ wherein $R_{200}$ and $R_{201}$ are independently selected from hydrogen and loweralkyl or the group $-NR_{200}R_{201}$ forms a nitrogen containing heterocyclic ring. These esters serve as pro-drugs of the compounds of the present invention and serve to increase the solubility of these substances in the gastrointestinal tract. These esters also serve to increase solubility for intravenous administration of the compounds. Other prodrugs include a compound of formula 1 and 2 wherein the hydroxyl group is functionalized with a substituent of the formula $-CH(R_g)OC(O)R_{181}$ or $-CH(R_g)OC(S)R_{181}$ wherein $R_{181}$ is loweralkyl, haloalkyl, alkoxy, thioalkoxy or haloalkoxy and $R_g$ is hydrogen, loweralkyl, haloalkyl, alkoxycarbonyl, aminocarbonyl, alkylaminocarbonyl or dialkylaminocarbonyl. The prodrugs of this invention are metabolized in vivo to provide the hydroxyl-substituted compound of formula 1 or 2. The preparation of the prodrug esters is carried out by reacting a hydroxyl-substituted compound of formula 1 or 2 with an activated amino acyl, phosphoryl, hemisuccinyl or acyl derivative as defined above. The resulting product is then deprotected to provide the desired pro-drug ester. Prodrugs of the compounds of formula 1 and 2 can also be prepared by alkylation of the hydroxyl group with (haloalkyl)esters, transacetalization with bis-(alkanoyl)acetals or condensation of the hydroxyl group with an activated aldehyde followed by acylation of the intermediate hemiacetal.

The following examples will serve to further illustrate the process of the invention.

EXAMPLE 1

(2S, 3R, 4R, 5S) -2,5-bis (benzyloxycarbonylamino) -3,4-dihydroxy-1,6-diphenylhexane

EXAMPLE 1a

L-Phenylalanine methyl ester hydrochloride

A 400 g (2.42 mol) sample of L-phenylalanine was slurried in 4 L of MeOH. To this was slowly added 240 mL of thionyl chloride, the temperature was allowed to increase, and the solution held at reflux for 16 hours. The solvent was removed to afford the title product as a white solid. The compound was taken directly to the next step.

EXAMPLE 1b

L-(N-Benzyloxycarbonyl)-phenylalanine methyl ester

The crude L-phenylalanine methyl ester hydrochloride from step 1a was dissolved in 4 L of chloroform and cooled to 0° C. To this was added with stirring 4 × 1 L portions of 20% sodium carbonate solution. The solution was stirred for an additional 15 min to complete the neutralization. The solution was cooled to 0° C., 400 mL (2.78 mol) of benzyl chloroformate was added slowly, and the reaction stirred for 2 hours at room temperature. The layers were separated, and the chloroform layer was washed with 2 L of 1N hydrochloric acid and dried over magnesium sulfate. The solvent was removed to leave the title compound as a viscous oil, which was taken directly to the next step.

EXAMPLE 1c

L-(N-Benzyloxycarbonyl)-phenylalaninol

A 2.42 L portion of 1M lithium aluminum hydride in THF was diluted with 1.2 L of THF and stirred under $N_2$ at 0° C. The crude L-(N-benzyloxycarbonyl)-phenylalanine methyl ester from step 1b was dissolved in 1.2 L of THF, and this solution was added to the first solution over a 30 minute period. The mixture was allowed to warm to room temperature and stirred for an additional hour. The reaction was quenched by careful addition of 92 mL of water, 92 mL of 15% NaOH, and 276 mL of water, the resultant gel was filtered, and the filter cake was washed thoroughly with hot ethyl acetate. The solvent was removed by evaporation under reduced pressure, and the resulting solid was recrystallized from 1:2 ethyl acetate:hexane, to afford 308 g of the title product; mp 89.2° C.; specific rotation −40.2° (c=0.50, methanol). A second crop of 106 g was obtained.

EXAMPLE 1d

L-(N-Benzyloxycarbonyl)-phenylalaninal

To 870 mL of dry methylene chloride was added 24.5 mL (350 mmol, 2 equiv.) of dry DMSO, and the solution was cooled to −60° C. under $N_2$. To this was added 131.2 mL (0.262 mmol, 1.5 equiv.) of 2M oxalyl chloride in methylene chloride over a 15 min period, taking care to maintain the temperature at −50° C. or lower, and the reaction was stirred at −60° C. for 15 min. Then 50.0 g (0.175 mol) of L-phenylalaninol, from step 1c above, in 200 mL of methylene chloride was added over a 20 min period, taking care to maintain the temperature at −50° C. or lower, and the reaction was stirred at −60° C. for 1 hour. Over a 15 min period was added 97 mL (0.700 mol, 4.0 equiv.) of triethylamine, taking care to maintain the temperature at −50° C. or lower, and the reaction was stirred at −60° C. for 15 min. To the reaction vessel was then added 163 g of citric acid in 550 mL of water over a 1 min period, with the cooling bath in place. The resulting slurry was stirred vigorously for 10 min. The mixture was diluted with 1 L of water and agitated vigorously, then the organic layer was separated and washed with 700 mL of water followed by 550 mL of water to which 150 mL of saturated sodium bicarbonate solution had been added. The organic solution was dried over magnesium sulfate, filtered and concentrated on a rotary evaporator. The title product was obtained as light yellow crystalline mass, which was immediately dissolved in methylene chloride and taken to the next step.

EXAMPLE 1e (2S,3R,4R,5S)-2,5-bis(benzyloxycarbonylamino)-3,4-dihydroxy-1,6-diphenylhexane To a flask containing 78.5 g (0.21 mol, 1.2 equiv.) of $VCl_3(THF)_3$ (prepared according to Manzer, *Inorg. Synth.*, 21, 135(1982)) was added 16.0 g (0.245 mol, 1.4 equiv.) of zinc dust and 400 mL of methylene chloride. The mixture was stirred for 1 hour under $N_2$, maintaining the reaction at room temperature with water bath cooling. To this was added the L-(N-benzyloxycarbonyl)-phenylalaninal, from step 1d, in 200 mL of methylene chloride, and the reaction was stirred at room temperature under $N_2$ for 16 hours. The reaction mixture was then added to 500 mL of 1N HCl, diluted with 500 mL of hot $CHCl_3$, and agitated vigorously for 2 min. The organic layer was separated and again washed with 1N HCl, separated and filtered. The filter cake was washed with hot acetone/$CHCl_3$. The solvents were removed under reduced pressure to obtain the crude product. This mixture of isomers was slurried in 1.25 L of acetone, 5 mL of conc. sulfuric acid was added and the mixture stirred for 16 hours. The slurry was filtered and the cake washed with 50 mL of acetone. The filtrate was concentrated to about 250 mL, diluted with 1 L of methylene chloride, washed $3\times$ with water and once with brine, then dried over magnesium sulfate and concentrated to give a viscous oil. The oil was taken up in 1 L of 1M methanolic HCl and stirred at room temperature for 2 hours. The resulting precipitate was isolated by filtration, washed with methanol and dried to give the isomerically pure title product as a white solid (26.7 g, second crop 8.3 g) ; mp 215°–216° C. $^1$H NMR ($d_6$-DMSO) $\delta$2.59 (dd, J=13, 5 Hz, 2H), 2.74 (dd, J=13, 9 Hz, 2H), 3.26 (br, 2H), 4.19 (m, 2H), 4.54 (m, 2H), 4.92 (m, 4H), 6.82 (d, J=9 Hz, 2H), 7.0–7.35 (m, 20H).

EXAMPLE 2

(2S,3R,4S,5S)-2,5-diamino-3,4-dihydroxy-1,6-diphenylhexane

EXAMPLE 2a (2S, 3R, 4R, 5S) -2,5-bis (benzyloxycarbonylamino)-3-acetyloxy-4-hydroxy-1,6-diphenylhexane A finely crushed sample of (2S,3R,4R, 5S)-2,5-bis (benzyloxycarbonylamino) -3,4-dihydroxy-1,6-diphenylhexane (235 g, 0.41 mol, from Example 1) was slurried in 6 L of acetonitrile. To this stirred mixture at room temperature was added triethylorthoacetate (3.0 equiv., 235 mL), followed by addition of methanesulfonic acid (17 mL) in one portion. After 45 min the small amount of material that had not dissolved was removed by filtration. Water (1 L) was added and the solution was stirred an additional 45 min. The filtrate was concentrated to a small volume, diluted with 2 L of ethyl acetate, and separated from the acidic aqueous layer. The organic layer was washed sequentially with 0.5 L of saturated $NaHCO_3$, 0.5 L of water, 0.5 L of brine, and dried over $MgSO_4$; then the solvent was removed to leave an oily solid. This residue was triturated with hexane, filtered, and dried under vacuum at 50° C. to give 243.5 g of the mono-acetate title product as an off-white powder; mp 130–131° C. $^1$H NMR ($CDCL_3$)$\delta$2.08 (s, 3H), 2.66 (m, 2H), 2.83 (m, 3H), 3.58 (m, 1H), 4.19 (m, 1H), 4.47 (m, 1H), 4.82 (d, J=9.6 Hz, 1H), 4.90–5.08 (m, 6H), 7.07–7.39 (m, 20H).

EXAMPLE 2b (2S,3R,4R,5S)-2,5-bis(benzyloxycarbonylamino)-3-acetyloxy-4-methylsulfonyloxy,-1,6,-diphenylhexane The mono-acetate (243.5 g, 0.40 mol, from Example 2a) was dissolved in 4 L of methylene chloride under $N_2$. To this stirred solution cooled to 0° C. was added DMAP (dimethylaminopyridine, 7.85 g) and triethylamine (333 mL, 6.0 equiv.). Finally, methanesulfonyl chloride (92.7 mL, 3.0 equiv.) was added over 30 min. This yellow solution was stirred for 45 min at 0° C. One liter of 2.0M HCl was poured into the reaction mixture, the mixture was stirred briefly, and the layers were separated. The organic layer was washed with 1 L of half-saturated aqueous $NaHCO_3$ and 1 L of water, dried with $MgSO_4$, and concentrated to give 321 g of the title product as a syrup. This material was taken directly to the next step. $^1$H NMR ($CDCL_3$)$\delta$2.13 (s, 3H), 2.54 (dd, J=14, 9 Hz, 1H), 2.66 (m, 2H), 2.74 (dd, J=14, 6 Hz, 1H), 3.03 (s, 3H), 4.70 (m, 2H), 4.85 (ABq, J=9 Hz, 4H), 4.99 (m, 3H), 5.21(d, J=9 Hz, 1H), 7.08–7.38 (m, 20H).

EXAMPLE 2c (4S,5R,6S)-tetrahydro-5-acetyloxy-6-((S)-1-benzyloxycarbonylamino-2-phenylethyl)-4-phenylmethyl-2H-1,3-oxazin-2-one The 321 g of crude mesylate from Example 2b was dissolved in 1.5 L of DMF. To this stirred solution at room temperature was added 2.5 mL of saturated aqueous $NH_4Cl$, and the resulting solution was heated at 122° C. for 12 hours, at which time conversion of starting material was complete. The DMF was removed by rotary evaporation under reduced pressure to give an orange syrup. This material was dissolved in 1.5 L of ethyl acetate and washed with $2\times300$ mL water, 500 mL of half-saturated aqueous $NaHCO_3$, 300 mL of brine, dried with $MgSO_4$, and concentrated to give 208 g of the title product as a crystalline mass. A sample was recrystallized from ethyl acetate/hexane to give off white needles. m.p. 140°–142° C. $^1$H NMR ($CDCl_3$)$\delta$2.16 (s, 3H) , 2.66 (dd, J=12, 9 Hz, 1H), 2.86 (m, 2H), 3.13 (dd, J=15, 3 Hz, 1H), 4.16 (m, 2H), 4.34 (m, 1H), 4.80 (m, 1 H), 5.02 (ABq, J=12 Hz, 2H), 5.09 (br s, 1H), 5.15 (br s, 1H), 7.13–7.40 (m, 15H).

EXAMPLE 2d (2S,3R,4S,5S)-2,5-diamino-3,4-dihydroxy-1,6-diphenylhexane

The crude oxazinone (approx. 200 g, from step 2c) was dissolved in 6 L of 1,4-dioxane with gentle warming. To this stirred warm solution was added 4 L of water followed by 629 g (5 equiv.) of barium hydroxide octahydrate, and the resulting mixture was heated at reflux for 11 hours. The reaction mixture was cooled and filtered to remove the $BaCO_3$ precipitate. The filtrate was concentrated to remove the dioxane, and the resulting aqueous suspension was extracted with $4\times500$ mL of methylene chloride. The combined methylene chloride extracts were dried with anhydrous $K_2CO_3$, and the solvent was removed to give the product as a tan solid. This material was recrystallized from ethyl acetate to give 86 g of the title compound as colorless needles, mp 126.5° C. $^1$H NMR ($CDCl_3$)$\delta$2.46 (dd, J=14, 9 Hz, 1H) , 2.61 (dd, J=14, 11 Hz, 1H), 3.02 (td, J=9, 3 Hz, 1H), 3.19 (dd, J=14, 4 Hz, 1H), 3.35–3.4 (m, 2H), 3.51 (t, J=9 Hz, 1H), 3.76 (dd, J=9, 3 Hz, 1H), 7.2–7.4 (m, 10H).

EXAMPLE 3

(S) -3-Methyl-2-[[methyl-(2-pyridinylmethyl)amino ]carbonyl]aminobutyric acid

EXAMPLE 3a 2-(Methylaminomethyl)-pyridine

A solution of 2-picolinaldehyde (107.11 g, 1 mol, a severe irritant) in 100 mL of methanol was added to 50 mL of methylamine, and the solution was shaken under $N_2$ for 2 hours. Pre-wetted 10% Pd/C (2.5 g) in 20 mL MeOH was added to the first solution, and the mixture was shaken under 4 arm of $H_2$ for 5 hours. The solution was filtered, the filter cake washed with methanol (2×100 mL), and the solution was filtered through a nylon membrane filter and concentrated in vacuo. Toluene was added, and the solution was concentrated in vacuo to afford 122 g of the title product as an orange oil; bp 80°–82° C.@8 mm Hg. NMR (CDCl$_3$) δ:2.00 (bs,1H), 2.49 (s,3H), 3.88 (s,2H), 7.18 (m, 1H), 7.32 (d,1H), 7.65 (dt,1H), 8.56 (m, 1H).

EXAMPLE 3b

N-(Phenyloxycarbonyl)-L-valine methyl ester

To a solution of 100 g (596 mmol) of L-valine methyl ester hydrochloride and 84.92 g (542 mmol) of phenylchloroformate in 600 mL of water and 600 mL methylene chloride at 0° C. was added 139.0 g of Na$_2$CO$_3$ (1.311 mol) in portions. After addition was complete the cooling bath was removed and the solution was stirred at ambient temperature for one hour. The organic layer was separated, 1.0 mL of N,N-dimethylethylenediamine (11.0 mmol) was added to the organic layer and the solution mixed for three minutes. The organic layer was washed with 100 mL of 1M potassium hydrogen sulfate solution. The organic layer was dried over magnesium sulfate, filtered and concentrated in vacuo to afford 135.65 g of the title compound as white crystalline solid; mp 59.1° C.

EXAMPLE 3c (S)-3-Methyl-2-[[methyl-(2-pyridinylmethyl)amino]carbonyl]aminobutyric acid methyl ester A solution of 2.68 g (22.0 mmol) of 2-(methylaminomethyl)-pyridine, from step 3a above, and 5.02g (20.0 mmol) of phenoxycarbonyl-L-valine methyl ester, from step 3b above, in 20 mL of 1,4-dioxane was purged with N$_2$. The solution was then heated at reflux for four hours under a N$_2$ atmosphere, then the solution was concentrated in vacuo. The resulting residue was dissolved in ethyl ether and extracted into 1N HCl. The aqueous layer was adjusted to about pH 9 with solid sodium carbonate and extracted twice with methylene chloride. The organic layers were combined and washed with 0.2M phosphate buffer at pH 7.0. The organic layer was dried over sodium sulfate, filtered and concentrated in vacuo, affording 5.17 g of the title product as a light yellow oil. NMR (CDCl$_3$)δ0.95 (dd,3H), 2.19 (m, 1H), 3.03 (s,3H), 3.72 (s,3H), 4.42 (dd, 1H), 4.54 (s,2H), 6.14 (bs,1H), 7.26 (m,2H), 7.70 (dt,1H), 8.56 (m, 1H).

EXAMPLE 3d (S)-3-Methyl-2-[[methyl-(2-pyridinylmethyl)amino]carbonyl]aminobutyric acid A solution of the urea methyl ester compound from step 3c (15.45 g, 55.4 mmol) in 55 mL MeOH and 110 mL THF was mixed at 0° C. with a lithium hydroxide solution (4.65 g, 111 mmol dissolved in 55 mL H$_2$O) and was stirred for one hour at room temperature. The organic solvents were evaporated in vacuo, and the resulting aqueous solution was extracted with ethyl ether. The aqueous layer was acidified with conc. HCl (9.25 mL, 111 mmol). To the acidic solution was added NaCl until it became saturated, whereupon it was extracted with 4×100 mL of 2:1 methylene chloride:THF. The organic layers were combined and dried over sodium sulfate, filtered and concentrated in vacuo. The pale residue was triturated with ethyl acetate and filtered, and the product was washed with ethyl acetate and dried to a constant weight to yield 12.50 g of the title product; mp 145.2° C.; NMR (CDCl$_3$)δ:1.01 (t,6H), 2.33 (m, 1H), 3.03 (s,3H), 4.21 (dd, 1H), 4.53 (dd, 2H), 6.70 (bs, 1H), 7.39 (m, 2H), 7.73 (dt, 1H), 8.55 (m, 1H).

EXAMPLE 4

Alternate preparation of (S)-3-Methyl-2-[[methyl-(2-pyridinylmethyl)amino]carbonyl]aminobutyric acid Example 4a N-(Phenyloxycarbonyl)-L-valine benzyl ester A slurry of 117.15 g (1 mol) of L-valine, 216.3 g (2.0 mol) of benzyl alcohol and 190.22 g (1.02 mol) of p-toluenesulfonic acid monohydrate in 450 mL of toluene was stirred and heated to reflux in an apparatus fitted with a Dean-Stark trap. After 20 hours the reaction was cooled to room temperature. The solution was poured into 1.5 L of ethyl ether, whereupon the p-toluenesulfonic acid salt of the benzyl ester of valine precipitated. To this thick suspension was added 1.3 L of water and solid sodium carbonate until the solution was alkaline. The aqueous phase was washed with ethyl ether, then the organic layers were combined and extracted with 1 L of 3M phosphoric acid. The organic solvent was discarded, and the aqueous layer was made basic by addition of 4.0M sodium hydroxide. Methylene chloride was added and the mixture was cooled to about 0° C., then 133.11 g (850 mmol) of phenylchloroformate was added over a two minute period. The reaction solution was stirred for one hour, the organic layer was separated and 5 mL of N,N-dimethylethylenediamine was added with mixing. The organic solution was washed once with 1 L of 1N HCl, dried over MgSO$_4$, filtered and concentrated in vacuo, to afford 231.5 g of the title product as a clear syrup. NMR (CDCl$_3$) δ:0.91 (d,3H), 1.02 (d,3H), 2.25 (m, 1H), 4.41 (q, 1H), 5.22 (dd,2H), 5.52 (d,1H), 7.12 (m,2H), 7.20 (m,2H), 7.39 (m, 6H).

EXAMPLE 4b (S)-3-Methyl-2-[[methyl-(2-pyridinylmethyl)amino]carbonyl]aminobutyric acid benzyl ester A solution of 80.5 g (660 mmol) N-methylpicolylamine and 196.3 g (600 mmol) of phenoxycarbonyl-L-valine benzyl ester, prepared in step 4a above, in 600 mL of 1,4-dioxane was purged with N$_2$. The solution was then heated at reflux for four hours under a N$_2$ atmosphere and concentrated in vacuo. The resulting residue was dissolved in ethyl ether and extracted twice with 2N HCl. The aqueous layers were combined and washed once with ethyl ether. The aqueous layer was adjusted to about pH 9 with solid sodium carbonate and extracted twice with methylene chloride. The organic layers were combined and washed twice with 0.2M phosphate buffer (pH 7.0). The organic layer was dried over sodium sulfate, filtered and concentrated in vacuo, to afford 192.2 g of the title product as a light yellow oil.

EXAMPLE 4c (S)-3-Methyl-2-[[methyl-(2-pyridinylmethyl)amino]carbonyl]aminobutyric acid To a solution of 40.2 g (113 mmol) of N-methylpicolylaminourea benzyl ester, from step 4b above, in 200 mL of methanol was added 4.0 g of 10% Pd/C. The resulting slurry was shaken under 4 atm. of H₂ for two hours. The reaction was filtered and the filtrate was concentrated in vacuo. The residue was triturated with ethyl acetate and concentrated to a thick paste. The residue was again triturated with ethyl acetate and filtered, and the product was washed twice with ethyl acetate and dried to a constant weight to afford 25.50 g of the title product; mp 145.2° C. NMR (CDCl₃)δ:1.01 (t, 6H), 2.33 (m, 1H), 3.03 (s, 3H), 4.21 (dd, 1H), 4.53 (dd, 2H), 6.70 (bs, 1H), 7.39 (m, 2H), 7.73 (dt, 1H), 8.55 (m, 1H).

EXAMPLE 5

(2S, 3R, 4S, 5S) -3,4-dihydroxy-2,5-bis-[[(S) -3-methyl-2-[[[methyl-(2-pyridinylmethyl)amino]carbonyl]amino]-1-oxobutyl-]amino]- 1,6-diphenylhexane To a slurry of 18.09 g (68.3 mmol) of (S)-3-Methyl-2-[[methyl-(2-pyridinylmethyl)amino]carbonyl-]aminobutyric acid, from Examples 3 or 4 above, and 9.93 g (71.37 mmol) of p-nitrophenol in 225 mL of anhydrous THF was added dropwise 14.02 g (68.0 mmol) of DCCI in 25 mL of THF. The reaction was stirred for two hours, and the DCU was filtered off and washed twice with THF. To the filtrate was added 9.31 g (31.03 mmol) of (2S,3R,4S,5S)-2,5-diamino-3,4-dihydroxy-1,6-diphenylhexane, from Example 2 above, and the solution was heated to reflux for ninety minutes. The solution was cooled to room temperature and 100 mL of 2N NaOH was added to hydrolyze the excess intermediate, then the solution was diluted with ethyl ether. The organic layer was separated and washed with 2N NaOH then extracted with 1N HCl. The aqueous extracts were combined and washed ethyl ether, then the pH of the aqueous solution was adjusted to about pH 10 with 2N NaOH. The alkaline solution was extracted twice with methylene chloride. The organic extract was washed with a 9:1 solution of 0.2M phosphate buffer:-brine, dried over sodium sulfate, filtered and concentrated in vacuo to yield 25.2 g of a slightly yellow solid. The solid was recrystallized from ethyl acetate/ethanol, washed with ethyl acetate and dried to a constant weight to afford 18.40 g of the title product; mp 167.1° C.; NMR (CD₃OD δ:0.77 (dd, 6H), 0.83 (dd, 6H), 1.89 (m, 1H), 1.99 (m, 1H), 2.64 (dd, 1H), 2.92 (m, 4H), 3.47 (dd, 1H), 3.60 (dd, 1H), 3.94 (d, 1H), 4.04 (d, 1H), 4.42 (t,1H), 4.53 (m,4H), 4.88 (s,6H), 7.22 (m,14H), 7.81 (tt,2H), 8.49 (m,2H).

EXAMPLE 6a

Alternate preparation of L-(N-Benzyloxycarbonyl)-phenylalaninal

A 1-L 3-necked Morton flask containing CBz-L-Phenylalaninol (8.56 g, 0.03 mol), TEMPO free radical (0.042 g, 0.0003 mol), and NaBr (3.19 g, 0.031 mol) in a bi-phasic mixture of toluene (90 mL)/ethyl acetate (90 mL) and water (15 mL) was immersed in a 0° C. ice water bath. With rapid mechanical stirring (1200 rpm), an aqueous solution of 0.35 M NaOCl (94 mL, 0.033 mol) containing NaHCO₃ (7.35 g, 0.0875 mol) was added dropwise over a period of 1 h and stirred for an additional 10 min. The aqueous layer was separated and washed with toluene (20 mL). The combined organic layers were washed with a solution of KI (0.25 g) dissolved in 10% aqueous KHSO₄ (40 mL). The iodine-colored organic layer was then washed successively with 10% aqueous sodium thiosulfate (20 mL), pH 7 phosphate buffer (0.2M, 50 mL) and saturated brine. Drying (Na2SO4) gave after filtration and concentration 8.50 g (96.6%) of the desired aldehyde as a white solid.

EXAMPLE 6b

Alternate Preparation of L-(N-Benzyloxycarbonyl)-phenylalaninal

A mixture of 2.5 equivalents of pyridine sulfurtrioxide, 2.0 equivalents of dimethytsulfoxide and methylene chloride was cooled to 0° C. To this mixture was added 2.5 equivalents of triethylamine. A solution of Cbz-L-Phenylalaninol (1.0) equivalents dissolved in a minimum amount of dimethylsulfoxide and methylene chloride was added slowly to the cold reaction mixture. After stirring for approximately 30 minutes, the reaction mixture was quenched by addition of a 15% aqueous citric acid solution. Extraction with methylene chloride, followed by washing the methylene chloride solution with water, drying over sodium sulfate and concentration, provided the desired product.

EXAMPLE 7

Alternate Preparation of L-(N-Benzyloxycarbonyl)-phenylalaninol

Cbz-L-Phenylalanine methyl ester (5.2 kg, 73.3 moles), sodium borohydroide (2.75 kg, 73.3 moles) and tetrahydrofuran (28 kg) were added to a suitably sized reactor. The contents of the reactor were stirred and the temperature maintained between 25°–35° C. by controlled addition of glacial acetic acid (4.44 kg, 73.9 moles). The reaction mixture was quenched in water (50 kg). Tetrahydrofuran was removed under vacuum and elevated temperatures. Ethyl acetate (35 kg) was added to the aqueous mixture and the solid borate salts were filtered away from the product mixture. The ethyl acetate layer was separated and the aqueous layer was extracted a second time using ethyl acetate (35 kg). The ethyl acetate layers were combined and extracted with 2% brine solution (35 kg) and dried over magnesium sulfate (2 kg) and concentrated to an oil. The desired product was crystallized from 1:2 ethyl acetate/heptane (60 kg) to afford a white solid.

EXAMPLE 8

Alternate Preparation of (2S,3R,4R,5S)-2,5-bis(benzyloxycarbonylamino)-3,4-dihydroxy-1,6-diphenylhexane 100 kg of the crude mixture of (2S,3R,4R,5S)-2,5-bis(-benzyloxycarbonylamino)-3,4-dihydroxy-1,6-diphenyl-hexane, (2S, 3R, 4S, 5S)-2,5-bis(benzyloxycarbonylamino)-3,4-dihydroxy-1,6-diphenylhexane and (2S,3S,4S, 5S)-2,5-bis(benzyloxycarbonylamino)-3,4-dihydroxy-1,6-diphenylhexane prepared using the coupling process of Example 1e was dissolved in 400 kg of acetone in a glass lined reactor reactor. To the acetone solution was added 14 kg of sulfuric acid over a period of not less than 5 minutes. The mixture was stirred at room temperature for not less than 12 hours. Then the mixture was cooled to 5° C. and stirred for not less than 2 hours. The reaction mixture was then filtered. The reaction vessel was rinsed with 160 kg of acetone and this acetone rinse was used to wash the filter cake. The acetone wash and the filtrate were combined and transferred to a glass lined reactor. The vessel that held the filtrate was rinsed with 750 kg of acetone. The acetone rinse was combined with the above-mentioned acetone wash and filtrate. 900 kg of distilled water was added and the mixture was heated to not more than 60° C. and stirred for not less than 18 hours. The mixture was then cooled to room temperature and let stand for 4 hours. The mixture was then filtered and the reaction vessel was rinsed with a mixture of 160 kg of acetone and 200 kg of distilled water. This acetone/water rinse solution was then used to wash the filter cake. The filter cake was dried under vacuum at 50° C. for at least 24 hours to give the desired product.

The foregoing is merely illustrative of the invention and is not intended to limit the invention to the disclosed embodiments. Variations and changes which are obvious to one skilled in the art are intended to be within the scope and nature of the invention which are defined in the appended claims.

What is claimed is:

1. A process for the preparation of the (3R,4S)-diol of the formula:

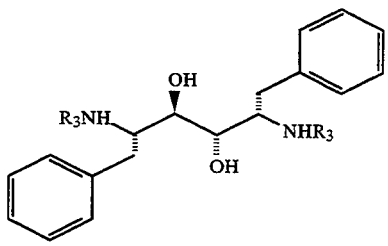

wherein at each occurrence $R_3$ is independently selected from hydrogen and an N-protecting group comprising (a) reaction of the (3R,4R)-diol of the formula:

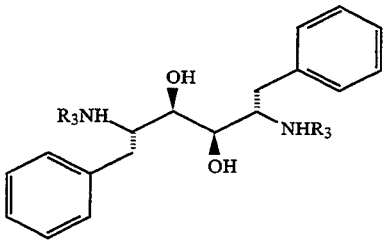

wherein $R_3$ is R*OC(O)— wherein R* is loweralkyl or benzyl with a compound of the formula $R_7C(OR_8)_3$ wherein $R_7$ is hydrogen, loweralkyl, phenyl or benzyl and $R_8$ is loweralkyl to provide a compound of the formula:

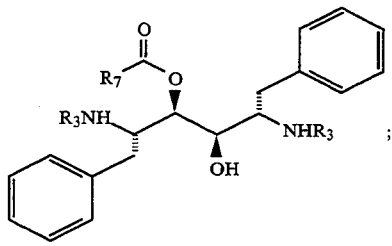

(b) reaction of the product of step a with RSO$_2$Cl or (RSO$_2$)$_2$O wherein R** is methyl, trifluoromethyl or 4-methylphenyl to provide the sulfonate derivative of the product of step a;

(c) heating the product of step b in an inert solvent to provide a compound of the formula:

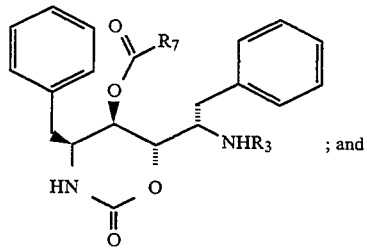

; and (d) reaction of the product of step c with a strong base.

2. The process of claim 1 wherein $R_3$ is carbonylbenzyloxy and $R_7$ is $CH_3$.

3. A process for the preparation of the (3R,4S)-diol of the formula:

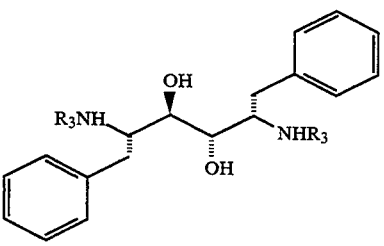

wherein at each occurrence $R_3$ is independently selected from hydrogen and an N-protecting group comprising (a) reaction of the (3R,4R)-diol of the formula:

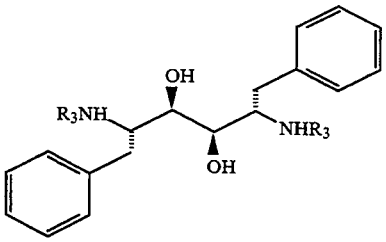

wherein $R_3$ is carbonylbenzyloxy with $CH_3C(OCH_2CH_3)_3$ to provide a compound of the formula:

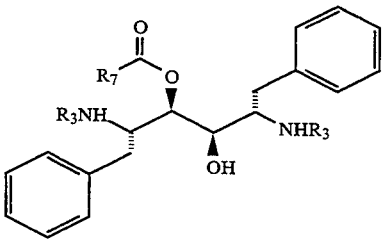

wherein $R_3$ is carbonylbenzyloxy and $R_7$ is $CH_3$;

(b) reaction of the product of step a with methanesulfonylchloride to provide the methansulfonate-derivative of the product of step a;

(c) heating the product of step b in an inert solvent to provide a compound of the formula:

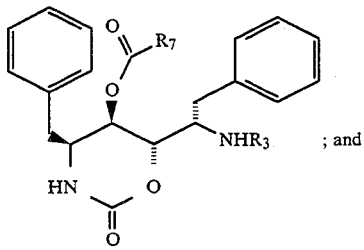

; and (d) reaction of the product of step c with a strong base.

4. A process for the preparation of the (3R,4S)-diol of the formula:

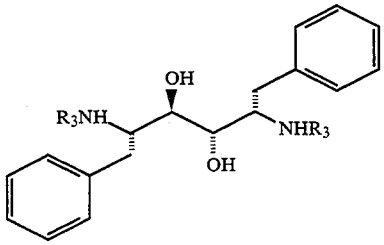

wherein $R_3$ is hydrogen comprising (a) reaction of the (3R,4R)-diol of the formula:

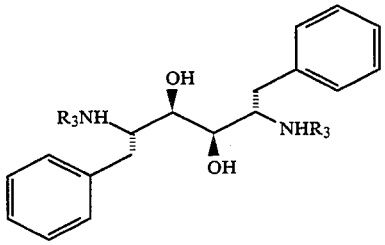

wherein $R_3$ is carbonylbenzyloxy with $CH_3C(OCH_2CH_3)_3$ to provide a compound of the formula:

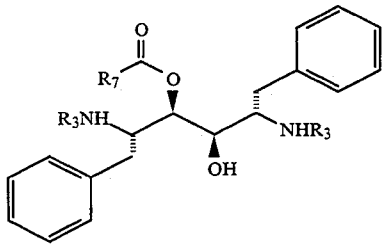

wherein $R_3$ is carbonylbenzyloxy and $R_7$ is $CH_3$;

(b) reaction of the product of step a with methanesulfonylchloride to provide the methansulfonate-derivative of the product of step a;

(c) heating the product of step b in dimethylformamide in the presence of aqueous ammonium chloride to provide a compound of the formula:

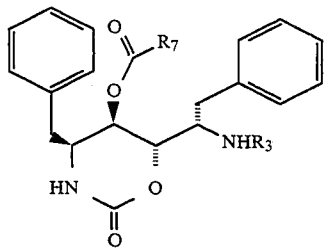

wherein $R_3$ is carbonylbenzyloxy and $R_7$ is $CH_3$; and (d) reaction of the product of step c with a strong base.

5. A process for the preparation of the (3R,4R)-diol of the formula:

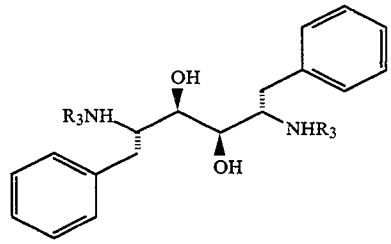

wherein $R_3$ is hydrogen or an N-protecting group comprising (a) reaction of N-protected L-phenylalaninal with a mixture of $VCl_3(THF)_3$ and zinc dust to produce a mixture of the (3R,4R)-, (3R,4S)- and (3S,4S)-diols of the formula:

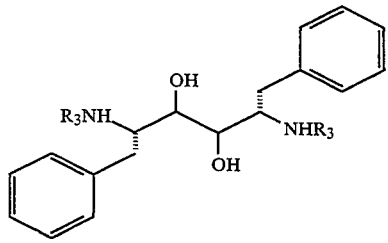

(b) reaction of the mixture of diols from step a with acetone and sulfuric acid to produce a mixture of the acetonides resulting from the (3R,4R)-, (3R,4S)- and (3S,4S)-diols;

(c) separation by selective crystallization of the acetonide resulting from the (3S,4S)-diol from the acetonides resulting from the (3R,4R)-diol and the (3R,4S)-diol;

(d) reaction of the mixture of acetonides resulting from the (3R,4R)- and (3R,4S)-diols with hydrochloric acid to selectively cleave the acetonide resulting from the (3R,4R)-diol, producing a mixture of the (3R,4R)-diol and the acetonide resulting from the (3R,4S)-diol; and (e) separation by selective crystallization of the (3R,4R)-diol.

6. The process of claim 5 wherein $R_3$ is carbonylbenzyloxy.

7. A process for the preparation of the (3R,4R)-diol of the formula:

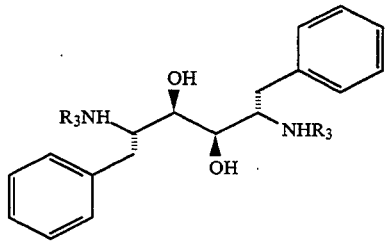

wherein $R_3$ is hydrogen or an N-protecting group comprising (a) reaction of N-protected L-phenylalaninal with a mixture of $VCl_3(THF)_3$ and zinc dust to produce a mixture of the (3R,4R)-, (3R,4S)- and (3S,4S)-diols of the formula:

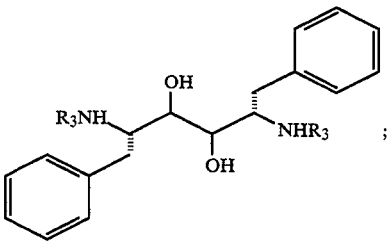

(b) reaction of the mixture of diols from step a with acetone and sulfuric acid to produce a mixture of the acetonides resulting from the (3R,4R)-, (3R,4S)- and (3S,4S)-diols;

(c) separation by selective crystallization of the acetonide resulting from the (3S,4S)-diol from the acetone/$H_2SO_4$ solution of the mixture of acetonides resulting from the (3R,4R)-diol and the (3R,4S)-diol;

(d) addition of water to the acetone/$H_2SO_4$ solution of the mixture of acetonides of the (3R,4R)-diol and the (3R,4S)-diol resulting from step c, followed by heating; and (e) separation by selective crystallization of the (3R,4R)-diol.

8. The process of claim 7 wherein $R_3$ is carbonylbenzyloxy.

9. A process for the preparation of the (3R,4R)-diol of the formula:

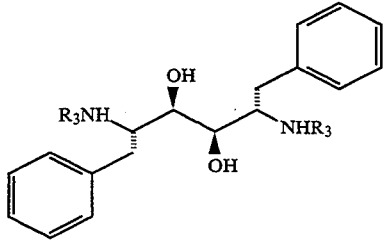

where $R_3$ is carbonylbenzyloxy comprising (a) reaction of N-carbonylbenzyloxy-L-phenylalaninal with a mixture of $VCl_3(THF)_3$ and zinc dust to produce a mixture of the (3R,4R)-, (3R,4S)- and (3S,4S)-diols of the formula:

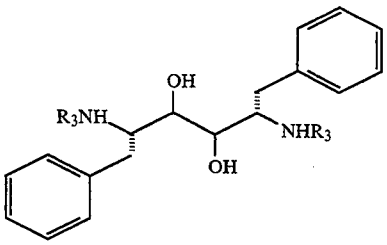

wherein $R_3$ is carbonylbenzyloxy;

(b) reaction of the mixture of diols from step a with acetone and sulfuric acid to produce a mixture of the acetonides resulting from the (3R,4R)-, (3R,4S)- and (3S,4S)-diols;

(c) separation by selective crystallization of the acetonide resulting from the (3S,4S)-diol from the acetonides resulting from the (3R,4R)-diol and the (3R,4S)-diol;

(d) reaction of the mixture of acetonides resulting from the (3R,4R)- and (3R,4S)-diols with hydrochloric acid to selectively cleave the acetonide resulting from the (3R,4R)-diol, producing a mixture of the (3R,4R)-diol and the acetonide resulting from the (3R,4S)-diol; and (e) separation by selective crystallization of the (3R,4R)-diol.

10. A process for the preparation of the (3R,4R)-diol of the formula:

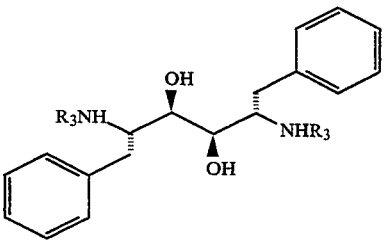

wherein $R_3$ is carbonylbenzyloxy comprising (a) reaction of N-carbonylbenzyloxy-L-phenylalaninal with a mixture of $VCl_3(THF)_3$ and zinc dust to produce a mixture of the (3R,4R)-, (3R,4S)- and (3S,4S)-diols of the formula:

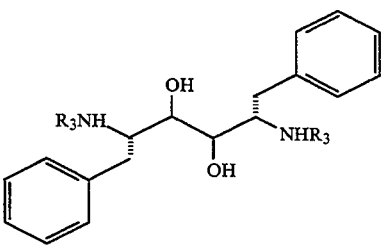

wherein $R_3$ is carbonylbenzyloxy;

(b) reaction of the mixture of diols from step a with acetone and sulfuric acid to produce a mixture of the acetonides resulting from the (3R,4R)-, (3R,4S)- and (3S,4S)-diols;

(c) separation by selective crystallization of the acetonide resulting from the (3S,4S)-diol from the acetone/H$_2$SO$_4$ solution of the mixture of acetonides resulting from the (3R,4R)-diol and the (3R,4S)-diol;

(d) addition of water to the acetone/H$_2$SO$_4$ solution of the mixture of acetonides of the (3R,4R)-diol and the (3R,4S)-diol resulting from step c, followed by heating; and (e) separation by selective crystallization of the (3R,4R)-diol.

* * * * *